(12) United States Patent
Bilke et al.

(10) Patent No.: US 7,807,196 B2
(45) Date of Patent: Oct. 5, 2010

(54) PROCESS FOR DRYING AMOXICILLIN

(75) Inventors: Hans W Bilke, Kiefersfelden (DE); Otto Daemon, Jenbach (AT); Franz X Schwarz, Worgl (AT)

(73) Assignee: Sandoz GmbH, Kundl (AT)

( * ) Notice: Subject to any disclaimer, the term of this patent is extended or adjusted under 35 U.S.C. 154(b) by 766 days.

(21) Appl. No.: 10/296,350

(22) PCT Filed: May 28, 2001

(86) PCT No.: PCT/EP01/06081

§ 371 (c)(1),
(2), (4) Date: May 6, 2003

(87) PCT Pub. No.: WO01/92268

PCT Pub. Date: Dec. 6, 2001

(65) Prior Publication Data

US 2003/0186956 A1 Oct. 2, 2003

(30) Foreign Application Priority Data

May 30, 2000 (AT) ................................ A 942/2000

(51) Int. Cl.
*A61K 9/20* (2006.01)
(52) U.S. Cl. ...................................... 424/465; 424/464
(58) Field of Classification Search ................. 424/454, 424/464
See application file for complete search history.

(56) References Cited

U.S. PATENT DOCUMENTS

| 3,674,776 A | | 7/1972 | Long et al. ................ 260/239.1 |
| 4,812,561 A | * | 3/1989 | Hamashima et al. ........ 540/222 |
| 5,874,063 A | * | 2/1999 | Briggner et al. |
| 5,958,471 A | * | 9/1999 | Schwarz et al. ................ 426/3 |

FOREIGN PATENT DOCUMENTS

| EP | 780393 | | 6/1997 |
| GB | 735455 | | 8/1955 |
| GB | 2005538 A | * | 4/1979 |
| GB | 2096599 | | 10/1982 |
| JP | 55-102585 | | 8/1980 |
| KR | 91-00418 | | 1/1991 |
| WO | WO 97/15579 | | 5/1997 |

OTHER PUBLICATIONS

Federal Register, vol. 63, No. 52, p. 13121 (1998).
Gerhartz, W., Ullman's Encyc. of Ind. Chem., pp. 4-20 and 4-21, (1988).
Patel et al., Pharm. Res., vol. 13, No. 4, pp. 588-593 (1996).
"Identification of Dimer Impurities in Ampicillin and Amoxicillin by Capillary LC and Tandem Mass Spectrometry," by Chi-Yu Lu and Chia-Hsien Feng, J. Sep. Sci. 2007, 30, 329-332.

* cited by examiner

*Primary Examiner*—Humera N Sheikh
(74) *Attorney, Agent, or Firm*—Luedeka, Neely & Graham, P.C.

(57) ABSTRACT

Process for drying amoxicillin (compositions), characterised in that a gas, which is inert towards amoxicillin (compositions) and having a relative humidity content which is greater than zero is used for drying.

7 Claims, No Drawings

PROCESS FOR DRYING AMOXICILLIN

The present invention relates to a drying process of pharmaceutically active compounds, e.g. amoxicillin and combinations of amoxicillin with a β-lactamase inhibitor, e.g. clavulanic acid.

Amoxicillin of formula

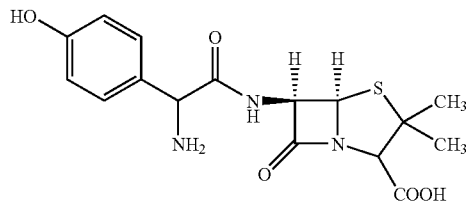

I e.g. described in the Merck Index, 12th Edition, item 617, is known as an antibacterial active ingredient. Amoxicillin may be used e.g. alone, or in combination, e.g. in combination with a β-lactamase inhibitor, such as clavulanic acid, e.g. described in the Merck Index 12th Edition, item 2402. A combination of amoxicillin and clavulanic acid e.g. in a pharmaceutical dosage form, such as in solid form, e.g. in the form of granules or in the form of a tablet for oral administration, is known and is obtainable commercially e.g. under the Trade name Augmentin®.

During the preparation of a pharmaceutical dosage form containing amoxicillin often a water drying process is involved. It is especially important to dry amoxicillin if it is present in a combination with a moisture-sensitive compound, e.g. with a β-lactamase inhibitor, such as clavulanic acid, since a moisture-sensitive compound can rapidly degrade in contact with humidity, e.g. water moisture. For drying of amoxicillin for example dry air has been used.

It has been found that when drying amoxicillin, e.g. with dry air, e.g. at room temperature, portions of an amoxicillin dimer, e.g. of formula

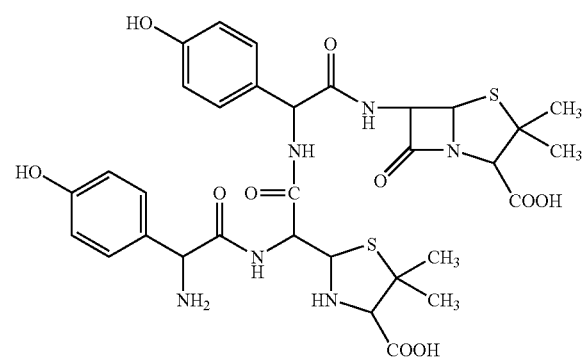

II may be formed.

Now, surprisingly, a process for drying amoxicillin has been found, in which the formation of an amoxicillin dimer, e.g. of formula II, can be reduced or prevented.

In one aspect, the present invention provides a process for drying amoxicillin, comprising drying amoxicillin with a gas, which is inert towards amoxicillin under the drying conditions and which gas has a relative humidity content of greater than zero, e.g. 1.5% and more, such as 1.5% to 4%.

Amoxicillin includes amoxicillin in any form, e.g. in the form of a solvate, e.g. a hydrate, such as a trihydrate and amoxicillin in the form of a salt, e.g. in the form of a sodium salt. Amoxicillin as used herein also includes amoxicillin alone or in combination. Amoxicillin in combination includes amoxicillin in combination with a second active compound, such as a pharmaceutically active compound; and/or
a β-lactamase inhibitor, which itself is not pharmaceutically active, or only to a small extent, but which inhibits the action of a β-lactamase, e.g. of micro-organisms such as bacterias; and thus may enhance the action of amoxicillin or a second pharmaceutically active compound when present.

Amoxicillin alone or in combination as used herein also includes a combination of amoxicillin alone or in combination with at least one pharmaceutically acceptable excipient, e.g. including a pharmaceutical composition comprising amoxicillin as an active ingredient, optionally comprising a second active compound, with at least one pharmaceutically acceptable excipient; e.g. in solid form, e.g. in the form of a powder, a granulate, in crystalline form, e.g. in compressed form, such as a granule or a tablet, e.g. including a non-filmed and a filmed tablet/granule, e.g. for oral administration.

A β-lactamase inhibitor includes e.g. clavulanic acid, e.g. in the form of a salt, e.g. an alkali metal salt, such as a potassium salt.

In another aspect the present invention provides a process for drying a combination of amoxicillin and a second active compound, such as a β-lactamase inhibitor, or for drying a pharmaceutical formulation comprising amoxicillin as an active ingredient, optionally further comprising a second active compound, and a pharmaceutically acceptable excipient, comprising drying said combination or said pharmaceutical formulation with a gas, which is inert towards the ingredients of said combination or of said pharmaceutical formulation under the drying conditions and which gas has a relative humidity content of greater than zero, e.g. of 1.5% and more, such as 1.5% to 4%.

Amoxicillin is preferably in the form of a trihydrate. A combination of amoxicillin with a second active compound is preferably a combination of amoxicillin and clavulanic acid. Clavulanic acid is preferably in the form of a potassium salt. Amoxicillin or amoxicillin in combination with a second active compound preferably is in the form of a pharmaceutical formulation further comprising at least one pharmaceutically acceptable excipient. A pharmaceutical formulation is preferably a solid dosage form. A solid dosage form is preferably an oral dosage form, e.g. a powder, tablet or granule, more preferably a tablet. Preferably amoxicillin is in the form of a trihydrate, in combination with clavulanic acid in the form of a potassium salt, formulated in an oral dosage form, e.g. a tablet.

In another aspect the present invention provides a process for drying a pharmaceutical composition comprising amoxicillin in the form of a trihydrate and clavulanic acid in the form of a potassium salt in combination with at least one pharmaceutically acceptable excipient, comprising drying said pharmaceutical formulation with a gas, which is inert towards the ingredients of said pharmaceutical formulation under the drying conditions and which gas has a relative humidity content greater than zero, e.g. 1.5% and more, such as 1.5% to 4%.

A process according to the present invention may be carried out by drying amoxicillin which contains humidity, e.g.

water moisture, e.g. stemming from a formulation procedure, such as granulation, is dried with a gas which is not dry but which has a relative humidity content greater than zero. It is essential that the gas used for drying is not used in a dry state. The relative gas humidity content is greater than zero, e.g. at least 0.5%, e.g. 0.5% to 10%, preferably 2% to 4%, e.g. (around) 3%. The relative gas humidity content corresponds to the water content of the gas used. The gas which may be used for drying is a gas that is inert towards amoxicillin, a second pharmaceutical compound and excipients of a pharmaceutical formulation under the drying conditions and is preferably air.

The temperature of the gas used upon drying is not critical and is higher than 0° C. and less than 100° C., preferably between 10° C. and 50° C., e.g. room temperature. During drying, bound hydrate water in amoxicillin is preferably not removed.

Drying may be carried out by contacting amoxicillin with the gas which has a relative humidity content of greater than zero until a desired equilibrium-moisture content in the form in which amoxicillin is dried is adjusted. A desired equilibrium-moisture content in the form, in which amoxicillin is dried includes an equilibrium moisture content of 5% and less, e.g. 3% and less, e.g. 1% and less, such as 0.05%, e.g. 0.05% to 5%, e.g. if amoxicillin is present in the form of a hydrate, e.g. a trihydrate.

The equilibrium-moisture content is a measure of the water that is freely available in amoxicillin and is available for exchange with the atmosphere. Therefore, the equilibrium moisture content is not the actual water content in amoxicillin. For example, a hydrate/crystal water portion e.g. in amoxicillin trihydrate does not count towards the size of the equilibrium-moisture content. A desired equilibrium-moisture content in amoxicillin in the form of a trihydrate excludes e.g. the water content of amoxicillin in the form of a trihydrate of ca. 12.9%, and includes moisture of the form in which amoxicillin is present upon drying, e.g. 5% and less.

Removal of the hydrate/crystal water during drying of amoxicillin in the form of a hydrate, may be undesirable. It has been found that when using a gas which has a relative humidity content of greater than zero, practically no hydrate/crystal water may be removed from amoxicillin in the form of a trihydrate, whereas when using a dry gas, such as dry air, hydrate/crystal water may be removed. Removal of bound hydrate water may accelerate amoxicillin dimer formation.

Drying may be carried out as appropriate, e.g. by a conventional process in which a solid is treated with a gas in order to dry it. Preferably, amoxicillin is brought into contact with the gas which has a relative humidity content of greater than zero in a container having an inlet opening and an outlet opening for the introduction and removal of gas, e.g. the gas is passed through the container in which amoxicillin is located. In a particular embodiment, a container is used, which has a double bottom. The gas is introduced between the two bottoms, flows through the container and is removed again at the top of the container. A gas, having a relative humidity content of greater than zero, e.g. of a specified relative moisture content, may be prepared as appropriate, e.g. by a conventional process. Preferably a stream of gas is passed through water, e.g. in a humidification chamber, and is mixed with a second, dry stream of gas. In that way a gas may be produced, which has a desired specified relative humidity content.

In another aspect the present invention provides a container for drying pharmaceutically acceptable compounds, e.g. amoxicillin, comprising a double bottom with an inlet where a drying gas having a humidity content of greater than zero is introduced and an outlet at the top of the container where the gas is removed, which is characterized in that the container is adapted with means for providing a drying gas having a humidity content of greater than zero. Means for providing a drying gas having a humidity content of greater than zero are e.g. a humidification chamber as mentioned above.

It has also been found that the formation of the amoxicillin dimer, e.g. of formula II, is independent of the rate of flow of the gas, which has a relative humidity content of greater than zero. In particular, in order to produce oral dosage forms such as tablets, which contain amoxicillin, a β-lactamase inhibitor and one or more pharmaceutically acceptable active ingredients, hereinafter called AmoxC tablets, an equilibrium-moisture content of >5% is generally necessary during production. On the other hand, it has been found that in order to have satisfactory stability in storage of the AmoxC tablets an equilibrium moisture content of 5% and less may be optimal, since clavulanic acid may degrade in formulations having an equilibrium moisture content of >5%. Thus, AmoxC tablets have to be dried after production to allow satisfactory stability in storage of 5% and less. Therefore, the process of the present invention is especially suitable for drying AmoxC tablets. It was also surprisingly found that, according to the process of the present invention to obtain a desired equilibrium-moisture content e.g. of 5% and less, when using amoxicillin in the form of a hydrate, e.g. a trihydrate, the amoxicillin may be dried such that upon drying practically no amoxicillin dimer, e.g. of formula II, is produced, e.g. 1% and less, such as 0.6% and less, e.g. 0.55% to 1%. One advantage of the process according to the present invention over conventional processes may include that during drying practically no crystal/hydrate water in amoxicillin in the form of a hydrate, e.g. trihydrate, is removed when adjusting a desired equilibrium-moisture content.

A pharmaceutical composition, such as a tablet, which contains amoxicillin in the form of a trihydrate, clavulanic acid in the form of a potassium salt and at least one pharmaceutical excipient, wherein the amoxicillin dimer, e.g. of formula II, content in amoxicillin is 1% and less, e.g. 0.6% and less, e.g. 0.55% to 1.0%, e.g. and having an equilibrium-moisture content of 5% and less, is new.

In another aspect, the present invention provides a pharmaceutical composition, e.g. an oral, pharmaceutical dosage form, such as a tablet, comprising amoxicillin in the form of a trihydrate, clavulanic acid in the form of a potassium salt and at least one pharmaceutical excipient, which is characterized in that said amoxicillin in said pharmaceutical composition contains less than 1% of an amoxicillin dimer, such as of formula II; e.g. and which has an equilibrium moisture content of 5% and less.

The content of amoxicillin dimer of formula II in amoxicilfin may be determined as appropriate, e.g. by HPLC. The relative humidity content of a gas and the equilibrium-moisture content in powders, granulates and tablets may be determined as appropriate, e.g. including a conventional process.

The following example illustrates but does in no way limit the present invention.

EXAMPLE 1

50-100 kg of film coated tablets each comprising 1004.3 mg amoxicillin trihydrate and 148.9 mg potassium salt of clavulanic acid corresponding to 875 mg amoxicillin and 125 mg clavulanic acid are filled into a drying container that is equipped with a double bottom, an air inlet at the bottom, an air outlet at the top, a humidification chamber for air and an electronic regulation unit to adjust the relative humidity of the drying air.

The tablets are flushed in the container with dried compressed air being adjusted to have a relative humidity of 2.5±0.5% at a flow rate of 12 m³/h until the equilibrium relative humidity of the tablets is below 5% at 25° C.

The content of dimeric amoxicillin determined by HPLC after the drying process is 0.9% per weight (content of dimeric amoxicillin in the starting material: 0.5% per weight).

COMPARATIVE EXAMPLE

The same process as described above in Example 1 is carried out wherein the dried compressed air is used directly without moistening, i.e. with a relative humidity of 0%. The content of dimeric amoxicillin determined by HPLC after the drying process is 4% per weight (content of dimeric amoxicillin in the starting material: 0.5% per weight).

The invention claimed is:

1. A process for drying tablets comprising amoxicillin trihydrate and potassium clavulanate, the process comprising the steps of:

placing the tablets into a drying container, flushing the container with dried, compressed gas that is inert towards amoxicillin and that has a relative humidity greater than 0% and less than about 10%, for a time until the tablets have an equilibrium-moisture content of less than about 5.0%, wherein the dried tablets comprise an amount of amoxicillin dimer which is less than about 1% of the amount of amoxicillin in the dried tablets.

2. The process of claim 1 wherein the gas is air.

3. The process of claim 1 wherein the relative humidity of the gas is less than about 5.0%.

4. The process of claim 3 wherein the relative humidity of the gas is less than about 3.0%.

5. The process of claim 1 wherein the relative humidity of the gas is 1.5% to 4.0%.

6. The process of claim 1 wherein the equilibrium moisture content is less than 3.0%.

7. A process for drying amoxicillin comprising drying amoxicillin with a gas that is inert towards amoxicillin and has a relative humidity content of 1.5% to 4%, wherein the amoxicillin dried by the process comprises less than about 1% of amoxicillin dimer.

* * * * *